(12) United States Patent
Addison et al.

(10) Patent No.: US 11,317,821 B2
(45) Date of Patent: *May 3, 2022

(54) SYSTEM AND METHOD FOR GENERATING AN ADJUSTED FLUID RESPONSIVENESS METRIC

(71) Applicant: Covidien LP, Mansfield, MA (US)

(72) Inventors: Paul Stanley Addison, Edinburgh (GB); Rui Wang, Livingston (GB); Scott McGonigle, Edinburgh (GB); James N. Watson, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 500 days.

This patent is subject to a terminal disclaimer.

(21) Appl. No.: 15/702,112

(22) Filed: Sep. 12, 2017

(65) Prior Publication Data
US 2018/0000360 A1 Jan. 4, 2018

Related U.S. Application Data

(63) Continuation of application No. 14/258,141, filed on Apr. 22, 2014, now Pat. No. 9,763,585.

(Continued)

(51) Int. Cl.
*A61B 5/02* (2006.01)
*A61B 5/0295* (2006.01)
(Continued)

(52) U.S. Cl.
CPC ............ *A61B 5/0295* (2013.01); *A61B 5/022* (2013.01); *A61B 5/0816* (2013.01); *A61B 5/14551* (2013.01)

(58) Field of Classification Search
CPC ..... A61B 5/0295; A61B 5/022; A61B 5/0816; A61B 5/14551
See application file for complete search history.

(56) References Cited

U.S. PATENT DOCUMENTS 5,995,855 A * 11/1999 Kiani ................. A61B 5/14551
600/310
6,129,675 A 10/2000 Jay
(Continued)

OTHER PUBLICATIONS

Cannesson, Maxime, et al. "Respiratory variations in pulse oximetry plethysmographic waveform amplitude to predict fluid responsiveness in the operating room." Anesthesiology: The Journal of the American Society of Anesthesiologists 106.6 (2007): 1105-1111 (Year: 2007).*

(Continued)

*Primary Examiner* — Andrey Shostak
(74) *Attorney, Agent, or Firm* — Shumaker & Sieffert P.A.

(57) ABSTRACT

The present invention relates to physiological signal processing, and in particular to methods and systems for processing physiological signals to predict a fluid responsiveness of a patient. A medical monitor for monitoring a patient includes an input receiving a photoplethysmograph (PPG) signal representing light absorption by a patient's tissue. The monitor also includes a perfusion status indicator indicating a perfusion status of the PPG signal, and a fluid responsiveness predictor (FRP) calculator programmed to calculate an FRP value based on a respiratory variation of the PPG signal. The FRP calculator applies a correction factor based on the perfusion status indicator.

20 Claims, 11 Drawing Sheets

Related U.S. Application Data

(60) Provisional application No. 61/939,103, filed on Feb. 12, 2014, provisional application No. 61/815,750, filed on Apr. 25, 2013.

(51) Int. Cl.
*A61B 5/022* (2006.01)
*A61B 5/08* (2006.01)
*A61B 5/1455* (2006.01)

(56) References Cited

U.S. PATENT DOCUMENTS

| | | | |
|---|---|---|---|
| 6,325,761 B1 | 12/2001 | Jay | |
| 7,044,917 B2 | 5/2006 | Arnold | |
| 7,976,472 B2 * | 7/2011 | Kiani | A61B 5/02416 600/507 |
| 8,048,040 B2 | 11/2011 | Kiani | |
| 8,221,319 B2 | 7/2012 | Lovejoy | |
| 8,251,912 B2 | 8/2012 | Shelley et al. | |
| 8,414,499 B2 | 4/2013 | Al-Ali et al. | |
| 2002/0161291 A1 * | 10/2002 | Kiani | A61B 5/0002 600/324 |
| 2006/0058690 A1 * | 3/2006 | Bartnik | A61B 5/7207 600/504 |
| 2009/0227882 A1 * | 9/2009 | Foo | A61B 5/0205 600/508 |
| 2009/0326393 A1 | 12/2009 | Sethi et al. | |
| 2010/0016680 A1 | 1/2010 | Addison et al. | |
| 2010/0017142 A1 | 1/2010 | Watson et al. | |
| 2010/0249559 A1 | 9/2010 | Lovejoy | |
| 2010/0324827 A1 * | 12/2010 | Addison | A61B 5/14551 702/19 |
| 2011/0021892 A1 | 1/2011 | Addison et al. | |
| 2011/0077474 A1 | 3/2011 | Huiku | |
| 2011/0319769 A1 * | 12/2011 | Hedberg | A61B 5/0452 600/481 |
| 2012/0029361 A1 * | 2/2012 | Addison | A61B 5/0205 600/484 |
| 2012/0271554 A1 * | 10/2012 | Shelley | A61B 5/02 702/19 |
| 2013/0080489 A1 | 3/2013 | Ochs et al. | |
| 2013/0226009 A1 | 8/2013 | Mestek et al. | |
| 2014/0058229 A1 | 2/2014 | Su et al. | |

OTHER PUBLICATIONS

Hertzman, Alrick B. "The blood supply of various skin areas as estimated by the photoelectric plethysmograph." American Journal of Physiology-Legacy Content 124.2 (1938): 328-340 (Year: 1938).*

International Search Report and Written Opinion of the International Searching Authority for application No. PCT/US 2014/034868, dated Jul. 10, 2014.

Cannesson et al, Relation between respiratory variations in pulse oximetry plethysmographic waveform amplitude and arterial pulse pressure in ventilated patients, Aug. 23, 2005. Critical Care 2005, vol. 9, No. 5, pp. R562-R568 (DOI 10.1186/cc3799).

Cannesson et al, Respiratory Variations in Pulse Oximetry Plethysmographic Waveform Amplitude to Predict Fluid Responsiveness in the Operating Room, Jun. 2007, Anesthesiology vol. 106, No. 6, pp. 1105-1111.

A. V. J. Challoner, Non-Invasive Physiological Measurements, Chapter 6. Photoelectric Plethysmography for Estimating Cutaneous Blood Flow, Academic Press 1979, pp. 125-151.

Dorlas et al, Photo-Electric Plethysmography as a Monitoring Device in Anaesthesia, 1985, British Journal of Anaesthesia, 57, pp. 524-530.

Michard et al, Clinical Use of Respiratory Changes in Arterial Pulse Pressure to Monitor the Hemodynamic Effects of PEEP, 1999, American Journal of Respiratory and Critical Care Medicine, vol. 159, pp. 935-939.

Natalini et al, Variations in Arterial Blood Pressure and Photoplethysmography During Mechanical Ventilation, Nov. 2006, International Anesthesia Research Society, vol. 3 No. 5, pp. 1182-1188.

Partridge, Use of Pulse Oximetry as a Noninvasive Indicator of Intravascular Volume Status, Oct. 1987, Journal of Clinical Monitoring, vol. 3, No. 4, pp. 263-268.

Poli et al, Pulse Oxymetry Wave Respiratory Variations for the Assessment of Volume Status in Patients Under Mechanical Ventilation, Abstract No. 350, Dec. 2004, Crit Care Med, vol. 32 , No. 12 (suppl.), p. A96.

Shamir, et al, Pulse Oximetry Plethysmographic Waveform During Changes in Blood Volume, 1999, British Journal of Anaesthesia 82 (2), pp. 178-181.

Addison, Paul S. PhD, A Review of Signal Processing Used in the Implementation of the Pulse Oximetry Photoplethysmographic Fluid Responsiveness Parameter, Dec. 2014—Anesthesia & Analgesia, vol. 119—Issue 6—pp. 1293-1306.

Broch, et al. "Accuracy of the pleth variability index to predict fluid responsiveness depends on the perfusion index." Acta Anaesthesiologica Scandinavica. 2011. p. 1-8.

International Preliminary Report on Patentability from International Application No. PCT/US2014/034868, dated Oct. 27, 2015, 5 pp.

Prosecution History from U.S. Appl. No. 14/258,141, dated Nov. 17, 2016 through May 16, 2017, 48 pp.

* cited by examiner

SYSTEM AND METHOD FOR GENERATING AN ADJUSTED FLUID RESPONSIVENESS METRIC

CROSS-REFERENCE TO RELATED APPLICATIONS

The present application is a continuation of U.S. application Ser. No. 14/258,141, filed Apr. 22, 2014, which claims priority benefits from U.S. Provisional Application No. 61/815,750, filed Apr. 25, 2013, and U.S. Provisional Application No. 61/939,103, filed Feb. 12, 2014, the contents of which are hereby expressly incorporated by reference.

FIELD

The present invention relates to physiological signal processing, and in particular to methods and systems for processing physiological signals to predict a fluid responsiveness of a patient.

BACKGROUND

Fluids are commonly delivered to a patient in order to improve the patient's hemodynamic status. Fluid is delivered with the expectation that it will increase the patient's cardiac preload, stroke volume, and cardiac output, resulting in improved oxygen delivery to the organs and tissue. Fluid delivery may also be referred to as volume expansion, fluid therapy, fluid challenge, or fluid loading.

However, improved hemodynamic status is not always achieved by fluid loading. Moreover, inappropriate fluid loading may worsen a patient's status, such as by causing hypovolemia to persist (potentially leading to inadequate organ perfusion), or by causing hypervolemia (potentially leading to peripheral or pulmonary edema).

Respiratory variation in the arterial blood pressure waveform is known to be a good predictor of a patient's response to fluid loading, or fluid responsiveness. Fluid responsiveness represents a prediction of whether such fluid loading will improve blood flow within the patient. Fluid responsiveness refers to the response of stroke volume or cardiac output to fluid administration. A patient is said to be fluid responsive if fluid loading does accomplish improved blood flow, such as by an improvement in cardiac output or stroke volume index by about 15% or more. In particular, the pulse pressure variation (PPV) parameter from the arterial blood pressure waveform has been shown to be a good predictor of fluid responsiveness. This parameter can be monitored while adding fluid incrementally, until the PPV value indicates that the patient's fluid responsiveness has decreased, and more fluids will not be beneficial to the patient. This treatment can be accomplished without needing to calculate blood volume or cardiac output directly. This approach, providing incremental therapy until a desired target or endpoint is reached, may be referred to as goal-directed therapy (GDT).

However, PPV is an invasive metric, requiring the placement of an arterial line in order to obtain the arterial blood pressure waveform. This invasive procedure is time-consuming and presents a risk of infection to the patient. Respiratory variation in a photoplethysmograph (PPG) signal may provide a non-invasive alternative to PPV. The PPG signal can be obtained non-invasively, such as from a pulse oximeter. One measure of respiratory variation in the PPG is the Delta POP metric, which is a measure of the strength of respiratory-induced amplitude modulations of the PPG. This metric assesses changes in the pulse oximetry plethysmograph, and is abbreviated as ΔPOP or DPOP.

Appropriate management of fluids can lead to improved patient outcomes, reduced length of stay, and reduced hospital cost. Thus there is a need for a reliable, noninvasive method to predict a patient's hemodynamic response to volume expansion, prior to fluid therapy.

SUMMARY

The present invention relates to physiological signal processing, and in particular to methods and systems for processing physiological signals to predict a fluid responsiveness of a patient. In an embodiment, a medical monitoring system receives a photoplethysmography (PPG) signal, representing light attenuated by the patient's tissue, and analyzes respiratory variations in the PPG signal in order to predict a fluid responsiveness of the patient. The system calculates a fluid responsiveness predictor (FRP) value, and optionally displays this value to a clinician for use in determining the patient's likely response to fluid therapy. The system also determines a perfusion status of the patient, and applies a correction to the FRP value when the patient is in a low perfusion state. This correction provides a robust FRP value with strong correlation to PPV, for non-invasive prediction of a patient's likely response to fluid loading.

In an embodiment, a medical monitor for monitoring a patient includes an input receiving a photoplethysmograph (PPG) signal representing light absorption by a patient's tissue. The monitor also includes a perfusion status indicator indicating a perfusion status of the PPG signal, and a fluid responsiveness predictor (FRP) calculator programmed to calculate an FRP value based on a respiratory variation of the PPG signal. The FRP calculator applies a correction factor based on the perfusion status indicator.

In an embodiment, a medical monitor for monitoring a patient includes an electrical input providing a photoplethysmography (PPG) signal responsive to light absorption by a patient's tissue. The monitor also includes a perfusion calculator programmed to calculate a perfusion value based on the PPG signal, a fluid responsiveness calculator programmed to calculate a fluid responsiveness value based on a respiratory variation of the PPG signal, and a scaling factor operating on the fluid responsiveness value to provide a scaled fluid responsiveness value based on the perfusion value.

In an embodiment, a medical monitor for monitoring vital signs of a patient includes an electrical input providing a photoplethysmography (PPG) signal responsive to light absorption by a patient's tissue, and a perfusion calculator programmed to calculate a percent modulation of the PPG signal. The monitor also includes a fluid responsiveness calculator programmed to calculate a Delta POP (DPOP) value based on a respiratory variation of the PPG signal. The monitor also includes a scaling unit operating on the DPOP value to provide a scaled DPOP when the percent modulation is below a threshold, and an output for providing the DPOP value or the scaled DPOP value to a display.

In an embodiment, a method for providing a non-invasive prediction of a patient's fluid responsiveness includes receiving a cardiac signal reflecting cardiac pulses of a patient, determining a respiratory modulation of the cardiac signal, determining a perfusion status of the patient, and outputting a scaled or corrected fluid responsiveness metric based on the perfusion status.

DETAILED DESCRIPTION

The present invention relates to physiological signal processing, and in particular to methods and systems for processing physiological signals to predict a fluid responsiveness of a patient. In an embodiment, a medical monitoring system receives a photoplethysmography (PPG) signal, representing light attenuated by the patient's tissue, and analyzes respiratory variations in the PPG signal in order to predict a fluid responsiveness of the patient. The system calculates a fluid responsiveness predictor (FRP) value, and optionally displays this value to a clinician for use in determining the patient's likely response to fluid therapy. The system also determines a perfusion status of the patient, and applies a correction to the FRP value when the patient is in a low perfusion state. This correction provides a robust FRP value with strong correlation to PPV, for non-invasive prediction of a patient's likely response to fluid loading.

Figure 1:
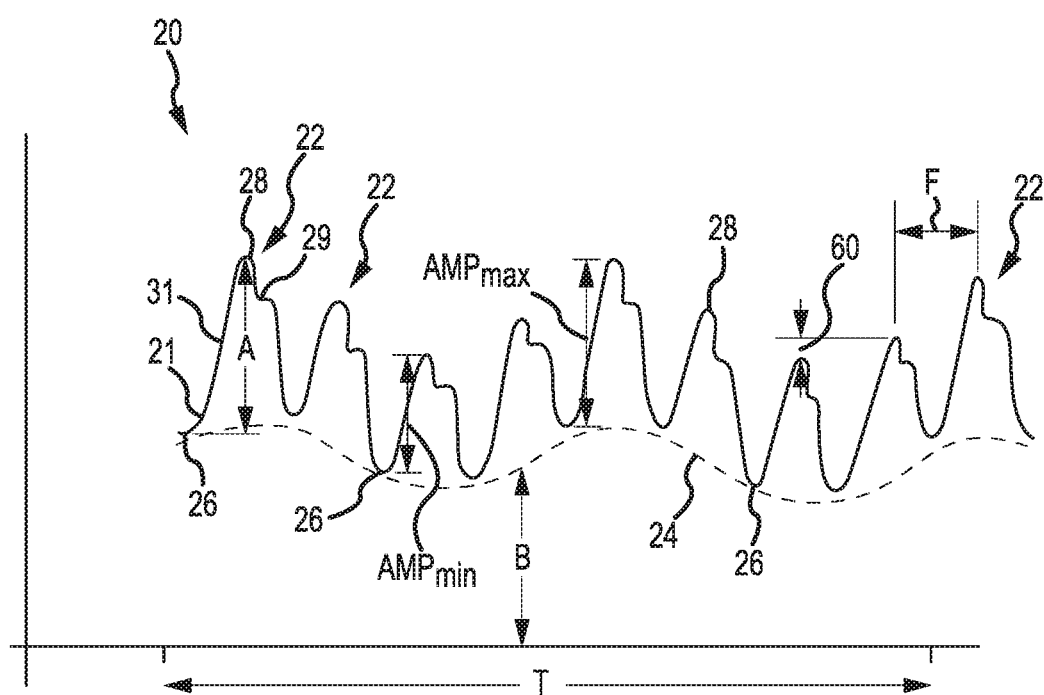
FIG. 1 illustrates a representation of a PPG signal, according to an embodiment of the present disclosure.

The photoplethysmography (PPG) signal can be obtained non-invasively by detecting light emitted into and emerging from a patient's tissue. An example of a device that can obtain a PPG signal is a pulse oximeter. Another example is a volume clamping device used to estimate blood pressure or cardiac output such as the Nexfin device (BMEYE, Amsterdam, Netherlands). An example of a PPG signal 20 obtained from a pulse oximeter is shown in FIG. 1. The PPG signal 20 may be output as a PPG waveform 21 which represents the absorption of light by a patient's tissue over time. The PPG waveform 21 includes cardiac pulses 22, where absorption of light increases due to the increased volume of blood in the arterial blood vessel due to the cardiac pulse 22. Each cardiac pulse 22 may be identified based on a valley 26, peak 28, dichrotic notch 29, and subsequent valley 26. The PPG signal includes an upstroke 31 with an amplitude A, measured from the preceding valley 26 to the peak 28. Other amplitude values may be derived from the PPG waveform, such as downstroke amplitude, average amplitude, or area under the pulse 22. The PPG waveform 21 also includes a baseline shift B indicating a baseline level 24 of the light absorption. The PPG waveform 21 modulates above the baseline 24 due to the arterial blood pulses. The PPG waveform 21 shown in FIG. 1 may be the PPG signal 112 of FIG. 6 (discussed below). In other embodiments, other types of signals other than a PPG signal may be used as the input signal 112, such as a capacitance signal reflective of cardiac pulses from the subject. Where a PPG signal is discussed herein, it should be understood that another type of cardiac signal, in particular a non-invasive cardiac signal, may be used.

For some patients, the PPG signal 20 is affected by the patient's respiration—inhaling and exhaling. A segment of a PPG waveform 21 during normal breathing is shown in FIG. 1. The waveform 21 includes the cardiac pulses 22. It should be noted that the number of cardiac pulses 22 per breath is not necessarily to scale, and may vary from patient to patient. Respiration (breathing in and out) may cause modulations in the PPG waveform 21.

One respiratory modulation is a modulation of the baseline B of the PPG waveform 21. The effect of the patient's breathing in and out causes the baseline 24 of the waveform 21 to move up and down, cyclically, with the patient's respiration rate. The baseline 24 may be tracked by following any component of the PPG waveform 21, such as the peaks 28, valleys 26, dichrotic notches 29, median value, or other value. A second respiration-induced modulation of the PPG signal 20 is a modulation of the amplitude A. As the patient breathes in and out, the amplitude A of each cardiac pulse 22 decreases and increases, with larger amplitudes tending to coincide with the top of the baseline shift B, and smaller amplitudes tending to coincide with the bottom of the baseline shift B (though the larger and smaller amplitudes do not necessarily fall at the top and bottom of the baseline shift). A third respiratory modulation is modulation of the frequency F between cardiac pulses. Each of these modulations may be referred to as a respiratory component of the PPG signal 20, or a respiratory-induced modulation of the PPG signal 20. It should be noted that a particular individual may exhibit only the baseline modulation, or only the amplitude modulation, or both. As referred to herein, a respiratory component of the PPG signal 20 includes any one of these respiratory-induced modulations of the PPG waveform 21, a measure of these modulations, or a combination of them.

The respiratory modulations of the PPG waveform 21 can be affected by a patient's fluid responsiveness. For example, a patient that is fluid responsive (for example, a hypovolemic patient) may exhibit relatively larger respiratory variations of the PPG waveform 21, while a patient that is not fluid responsive may exhibit relatively smaller respiratory variations of the PPG waveform 21. When a patient loses fluid, the respiratory variations present in the patient's PPG signal 20 tend to increase. As an example, when the patient's fluid volume is low, the arterial system exhibits larger compliance and thus expands more with each cardiac pulse, relative to the baseline 24. Both the baseline modulation and the amplitude modulation may become more pronounced when a patient's fluid volume decreases. Thus, larger respiratory modulations may indicate that a patient is in need of fluids, while smaller respiratory modulations may indicate that a patient is not in need of fluids. The respiratory modulations of the PPG signal 20, such as the PPG waveform 21, may be identified and used to predict a patient's fluid responsiveness.

In an embodiment, a medical monitoring system receives a PPG signal and calculates a fluid responsiveness predictor (FRP) based on the PPG signal. In an embodiment, the FRP is a measure of a patient's likelihood of response to fluid therapy. As an example, the FRP represents a prediction of whether such fluid therapy will improve blood flow within the patient. In an embodiment, the FRP is a metric that reflects a degree of respiratory variation of the PPG signal. One example of an FRP metric is a measure of the amplitude modulations of the PPG signal, such as Delta POP (DPOP or ΔPOP, defined below). In other embodiments, the FRP metric is a measure of the respiratory variation of the PPG, such as a measure of the baseline modulation of the PPG, or other suitable metrics assessing the respiratory modulation of the PPG. For example, an FRP may be based on the amplitudes or areas of acceptable cardiac pulses 22 within a particular time frame or window. The minimum amplitude of the cardiac pulses 22 may be subtracted from the maximum amplitude then divided by an average or mean value. Alternatively, an FRP may be derived from a frequency of cardiac pulses 22 within a time frame or window. For example, a modulation or variation in frequency among two or more cardiac pulses 22 may be used to derive an FRP. In general, the FRP may be based on one or more respiratory variations exhibited by the PPG signal 20. Further, an FRP may be determined through the use of wavelet transforms, such as described in U.S. Patent Application Publication No. 2010/0324827, entitled "Fluid Responsiveness Measure," which is hereby incorporated by reference in its entirety.

In an embodiment, DPOP is used as the FRP. The DPOP metric is calculated from the PPG waveform 21 for a particular time window as follows:

$$DPOP=(AMP_{max}-AMP_{min})/AMP_{ave} \qquad (1)$$

where $AMP_{max}$ represents the maximum upstroke amplitude (amplitude from a pulse minimum to a pulse maximum) during the time window (such as time window T in FIG. 1), $AMP_{min}$ represents the minimum upstroke amplitude during the time window, and $AMP_{ave}$ is the average of the two, as follows:

$$AMP_{ave}=(AMP_{max}+AMP_{min})/2 \qquad (2)$$

In other embodiments, $AMP_{max}$ and $AMP_{min}$ may be measured at other locations of the PPG, such as within or along a pulse. DPOP is a measure of the respiratory variation in the AC portion of the PPG signal. DPOP is a unitless value, and can be expressed as a percentage. In an embodiment, the time window is one respiratory cycle (inhalation and exhalation). In an embodiment, the time window is a fixed duration of time that approximates one respiratory cycle, such as 5 seconds, 10 seconds, or another duration. In other embodiments, the time window may be adjusted dynamically based on the patient's calculated or measured respiration rate, so that the time window is approximately the same as one respiratory cycle. A signal turning point detector may be used to identify the maximum and minimum points in the PPG signal, in order to calculate the upstroke amplitudes. In some embodiments, $AMP_{max}$ and $AMP_{min}$ may be calculated by identifying a maximum value and a minimum value within a cardiac pulse window, and calculating a difference between those values. This difference may correspond with an upstroke or a downstroke, for example.

To assess the usefulness of DPOP as a fluid responsiveness predictor, it can be compared with PPV (pulse pressure variation), a metric that is obtained from the invasive arterial pressure waveform and that is known to reliably indicate a patient's fluid responsiveness. DPOP and PPV have the same mathematical formulation, but are taken from different signals (DPOP from the PPG signal, and PPV from the invasive arterial pressure signal).

In comparing the PPV and DPOP metrics over historical patient data, DPOP is seen to deviate from PPV at low perfusion values. DPOP correlates well with PPV at higher perfusion values, but the correlation becomes skewed at lower perfusion values. Perfusion represents a measure of the amount of blood in the vascular bed, or the extent of blood flow to the patient's tissue and extremities. A well-perfused patient has good blood flow to the extremities, while a poorly-perfused patient has constricted or reduced blood flow (such as due to a cold environment or low arterial compliance).

Further analysis of this effect reveals that a patient's perfusion status affects the correlation between DPOP and PPV. The perfusion status may be represented by a perfusion metric, such as a metric that measures the relative amplitude of the AC or arterial component of the signal (such as the cardiac pulses 22 in FIG. 1) with respect to the DC or baseline component. The relative strength of amplitude of this modulating portion of the PPG signal compared to the baseline value is an indication of the patient's perfusion status. For example, a well-perfused patient tends to exhibit stronger, larger arterial pulses, with respect to the DC or baseline value of the PPG, than a poorly-perfused patient. A patient with poor perfusion tends to exhibit weaker or smaller pulses, with respect to the baseline. The perfusion metric may include trends in perfusion over time.

In an embodiment, a monitoring system modifies the FRP metric, such as DPOP, based on a perfusion status indicator, which indicates a perfusion status of the patient. In an embodiment, the perfusion status indicator is a modulation metric, such as a percentage modulation (Pmod) of the PPG signal. In an embodiment, Pmod is calculated as follows:

$$Pmod=AC/DC \qquad (3)$$

where AC is the amplitude of the AC portion of the PPG signal (such as an upstroke, downstroke, or cardiac pulse amplitude, or a combination or average of such amplitudes), and DC is the amplitude of the baseline portion of the PPG signal (such as the value, or average value, of the baseline level 24 in FIG. 1). In an embodiment, AC is $AMP_{ave}$ from equation (1) above, and DC is an average value of the baseline 24 over the same time window in which $AMP_{ave}$ is calculated. Pmod may be calculated as an instantaneous amplitude divided by an instantaneous baseline, or a mean (or other average) amplitude value divided by a mean (or other average) baseline value.

Pmod is a measure of the relative amplitude of one or more cardiac pulses 22 (or an average of pulses) with respect to the baseline 24. Pmod gives an indication of the perfusion status of the patient, as a well-perfused patient typically exhibits a larger Pmod (as the AC amplitude is a larger fraction of the DC amplitude) and a poorly-perfused patient typically exhibits a smaller Pmod. In various embodiments, a PPG signal from a well-perfused patient may exhibit a Pmod greater than 3%. A PPG signal from a more poorly-perfused patient may exhibit a Pmod equal to or less than 3%. In other embodiments, other thresholds are used, such as 1%, 2%, 3%, 4%, 5%, or approximately those numbers.

In other embodiments, perfusion metrics other than Pmod may be used, such as, for example, a perfusion index, or changes in peak-to-peak amplitude 60 of the PPG waveform 21 with respect to the baseline (shown in FIG. 1).

In an embodiment, a patient monitoring system determines a modulation metric and adjusts the FRP based on the modulation metric, to adjust for errors in the FRP at low perfusion. For example, the system determines Pmod and adjusts the DPOP metric when Pmod indicates low perfusion, in order to better correlate DPOP with PPV.

Figure 2:
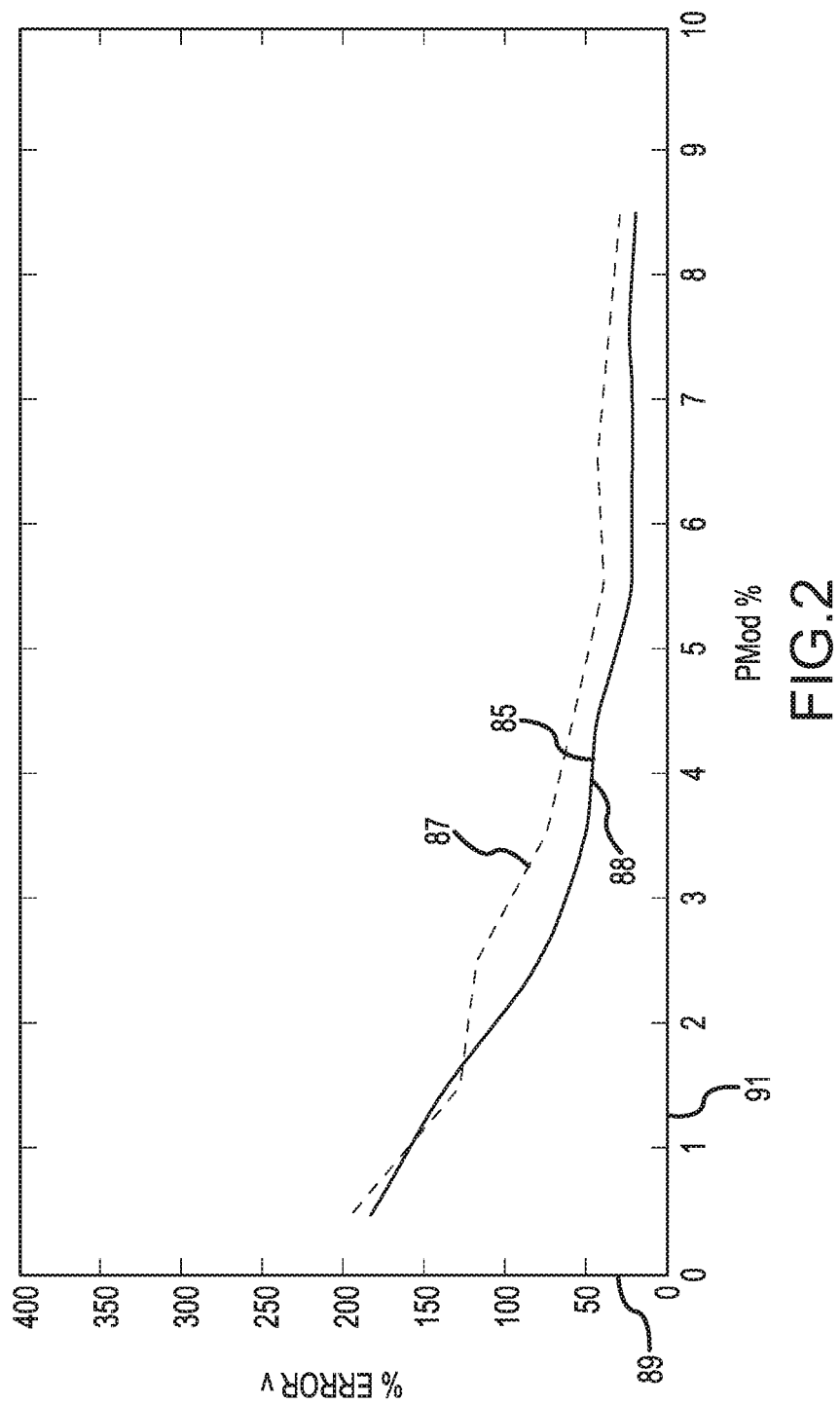
FIG. 2 illustrates a chart of correlation error versus percent modulation of a PPG signal, according to an embodiment of the present disclosure.

FIG. 2 illustrates a plot of the percent error between DPOP and PPV (on the vertical axis 89), plotted against the percent modulation (Pmod) of the PPG signal (on the horizontal axis 91). To calculate the error, DPOP and PPV were each normalized to a respective threshold (for example, 13% for PPV and 15% for DPOP), and then the error was calculated as the percentage that the normalized DPOP overestimated the normalized PPV. In FIG. 2, both the mean error 85 and the standard deviation error 87 are shown. The plot reveals an increasing error between DPOP and PPV as Pmod decreases. The patient's perfusion affects the correlation between DPOP and PPV. At lower perfusion values (indicated by lower Pmod values), the error between PPV and DPOP increases, as the two metrics deviate from each other. Study of the PPG signal indicates that, as perfusion lowers, there is a differentially faster decrease in the DPOP denominator (the average amplitude value) than the DPOP numerator (the modulation of the amplitude; the difference between the maximum and minimum amplitudes in a time window). This results in an increased DPOP value. Thus, as perfusion lowers, the DPOP value increases relative to the PPV value.

In particular, the mean error between PPV and DPOP is seen to increase below about 3% modulation. In an embodiment, low perfusion is defined as pulse amplitudes less than about 3% of the PPG baseline. In other embodiments, another threshold such as 1%, 2%, 4%, or 5% is used.

In an embodiment, the monitoring system uses the relationship shown in FIG. 2 to correct DPOP at low perfusion values. The system determines Pmod from the PPG signal, and determines the corresponding expected mean error from FIG. 2. The system then uses this expected mean error to apply a correction factor to the calculated value of DPOP, to decrease DPOP proportionately. The corrected DPOP value correlates better with PPV, and thus provides a better prediction of a patient's fluid responsiveness. For example, in an embodiment, when Pmod is above 3% (or another suitable threshold), no correction factor is applied. When Pmod is at or below 3%, the DPOP values are scaled according to the error shown in FIG. 2. For example, at a PMod 88 of approximately 2%, there is a mean error of approximately 100%. In order to accommodate for a 100% error, the fluid responsiveness predictor may then be reduced by 50% (for example, reduced from 20% to 10%). In an embodiment, the expected error is multiplied by a constant or weight before being applied to the DPOP value. It should be noted that the chart of FIG. 2 is merely exemplary, and the relationship between percentage error and PMod may be different than shown.

Based on empirical studies of the error between DPOP and PPV at low perfusion values, a relationship between error and perfusion status (PS) may be determined and used to correct DPOP. An example relationship is as follows:

$$FRP_{mod}=(x+y \cdot PS)FRP_0 \quad (4)$$

where x and y are constants that may be derived empirically, $FRP_{mod}$ represents the modified FRP, $FRP_0$ is the original FRP from equation (1), and PS is a perfusion status metric. In an embodiment, the FRP is DPOP, and PS is a modulation measure such as Pmod.

Accordingly, in an embodiment, the system calculates DPOP as follows: for Pmod>3%, DPOP is calculated according to equation (1) above, and for Pmod≤3%, DPOP is calculated according to equation (1) above and then modified according to equation (4) above. Thus, in an embodiment, a correction factor applied to an FRP calculated at a particular time is based on an expected error between PPV and the FRP at that particular time. The expected error may be obtained from a chart such as the one shown in FIG. 2, or from a lookup table or may be summarized by a formula from which the expected error can be calculated analytically. The chart in FIG. 2 may be obtained from historical patient data, simulated data, or a patient's individual medical history. Alternatively, a best fit line or polynomial function may be determined to quantify the error/Pmod relationship, and then used to determine the appropriate correction factor for the FRP.

While the examples above discuss the correction factor applied to DPOP, other FRP metrics may be used and corrected accordingly. For example, amplitude values and/or modulations, or baseline values and/or modulations from the PPG signal, or various respiratory components of the PPG signal may be scaled according to expected error, in order to provide a corrected FRP metric.

Figure 3A:
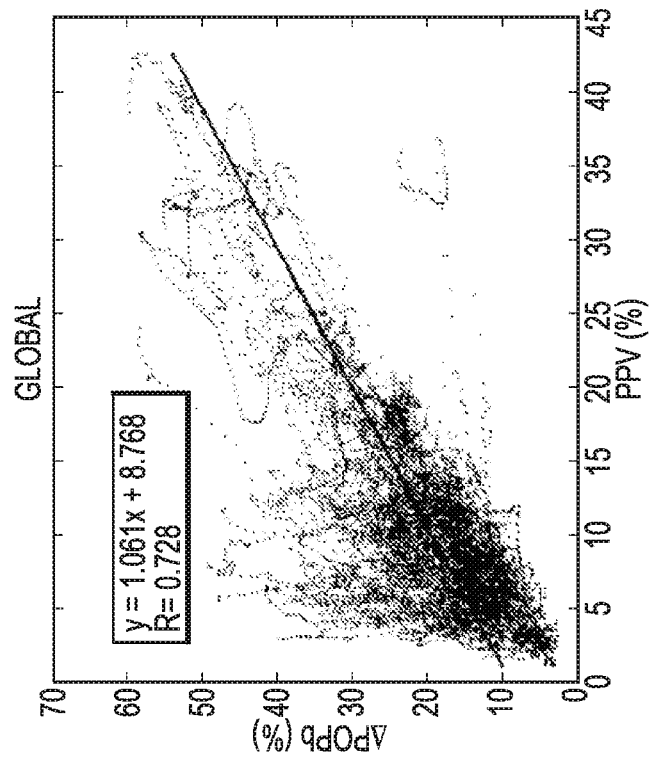
FIG. 3A illustrates a correlation plot of DPOP and PPV prior to implementing a correction for low perfusion data, according to an embodiment of the present disclosure.
Figure 3B:
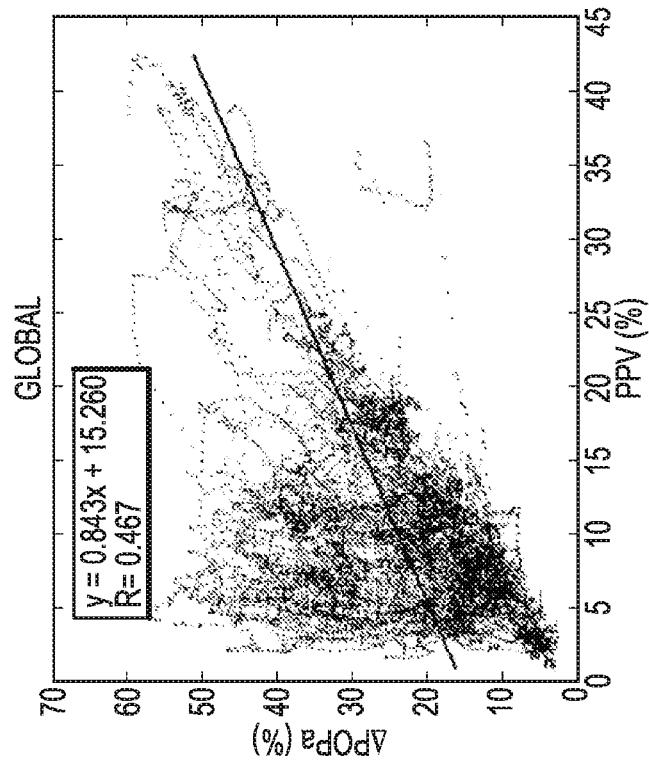
FIG. 3B illustrates a correlation plot of DPOP and PPV after implementing a correction for low perfusion data, according to an embodiment of the present disclosure.

FIGS. 3A and 3B illustrate the effect of applying a low perfusion correction to a historical data set. FIG. 3A plots the correlation between PPV (on the x-axis) and DPOP (on the y-axis) without any correction for low perfusion. A best fit line is applied, with a correlation coefficient R of 0.467. FIG. 3B plots the correlation between PPV and DPOP after a correction factor is applied according to Equation (4), with Pmod as the perfusion status indicator. A best fit line is applied, with an R value of 0.728, showing an improved correlation compared to FIG. 3A.

Figure 4A:
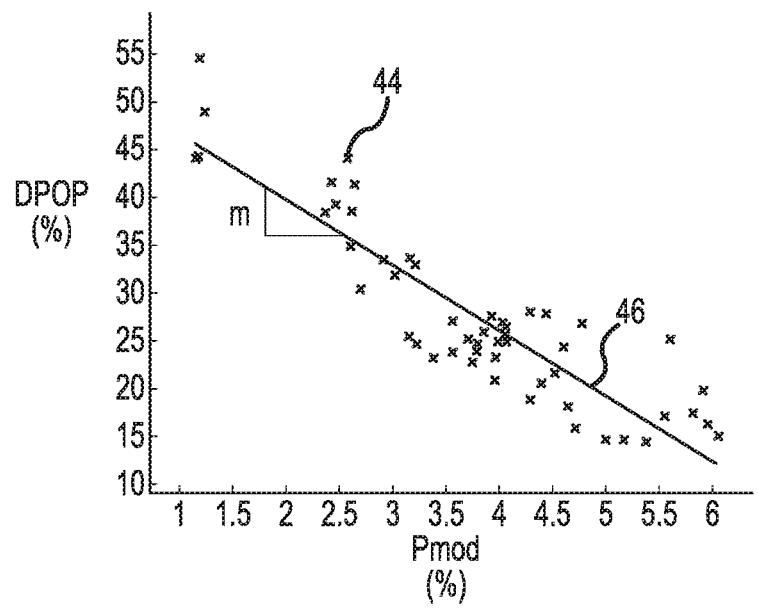
FIG. 4A illustrates a scatter plot relating DPOP with percent modulation of a PPG signal, according to an embodiment of the present disclosure.
Figures 4B, 4C:
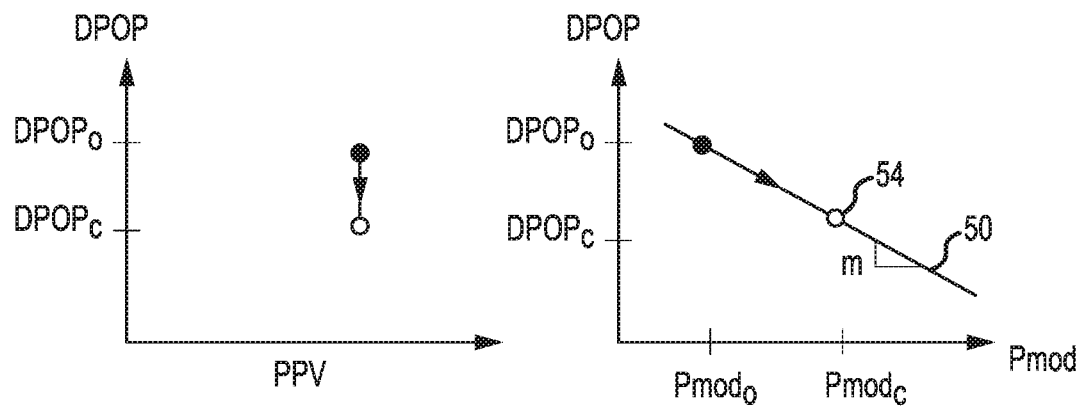
FIG. 4B illustrates a chart that represents a relationship between DPOP and Pmod, according to an embodiment of the present disclosure.
FIG. 4C illustrates a chart that represents a relationship between DPOP and PPV, according to an embodiment of the present disclosure.

Another embodiment for correcting an FRP value based on a perfusion status indicator is illustrated in FIGS. 4A, 4B, and 4C. FIG. 4A illustrates a scatter plot of DPOP (y-axis) and Pmod (x-axis) data points 44 taken from a PPG signal from a patient over several minutes. A downward sloping best fit trend line 46 with slope m illustrates the trend in the data points 44. As shown, as Pmod decreases, DPOP increases. For example, a DPOP value of approximately 45% corresponds to a PMod of approximately 1.25%, while a DPOP value of approximately 15% corresponds to a PMod of approximately 6%. The relationship between DPOP and PMod may be expressed according to the following equation:

$$DPOP=m \cdot Pmod+C \quad (5)$$

where DPOP (or other FRP metric) and Pmod (or other perfusion metric) may be calculated as described above, m is the slope or gradient of the trend line 46, and C is a constant. The constant C may be an empirical value derived from clinical studies of one or more patients.

The slope or gradient m of the trend line 46 is based on the data points 44. For example, one or more patients may be monitored and the data points 44 plotted to determine the trend line 46, which may then be used to determine the slope or gradient m. Optionally, a single patient may be studied over one or more time periods to plot the data points 44 and determine the trend line 46. Alternatively, an assumed or known slope or gradient m, such as derived through observations, clinical studies, and/or historical data may be used.

In an embodiment, the slope m is used to correct an FRP value at low perfusion. For example, the slope m may be used to correct a DPOP value, as shown in FIGS. 4B and 4C. In FIG. 4B, a corrected $Pmod_c$ and corresponding $DPOP_c$ are shown at point 54. When Pmod drops from $Pmod_c$ to $Pmod_0$, DPOP increases from $DPOP_c$ to $DPOP_0$. The relationship is shown along line 50, with slope m. However, as shown in FIG. 4C, PPV remains the same, even as DPOP increases from $DPOP_c$ to $DPOP_0$. Accordingly, a correction factor is applied to move the DPOP value back to $DPOP_c$, to remove the effect of the reduced Pmod on the DPOP value. This correction can be accomplished based on the slope m, as follows:

$$DPOP_c = DPOP_0 - m(Pmod_0 - Pmod_c) \quad (6)$$

Equation 5 or Equation 6 may be used for this calculation. This adjustment takes out changes in DPOP due to changes in Pmod. In an embodiment, a particular value of Pmod is chosen as the target $Pmod_c$ (such as, for example, 6%, 5%, 4%, or 3%), and DPOP values are adjusted to the corresponding $DPOP_c$ value at that $Pmod_c$. The $DPOP_c$ may be determined by moving along the line 50 to a point 54 that coincides with the target $PMod_c$.

The relationship given in Equation 5 or 6 may be patient-specific, or may be predetermined, such as based on historical or clinical data. As an alternative to using the equation given in Equation 5 or 6, the relationship between $DPOP_c$ and Pmod values may be represented by a non-linear polynomial function, or by a series of piecewise functions, or another type of mapping (non-parametric, non-linear, or heteroassociative), or the relationship may be learned by a neural network.

It should be noted that while Equations 4 and 6 above operate on $FRP_0$ or $DPOP_0$, the correction may be applied to the inputs to DPOP (or other FRP), such as the AMPmax and AMPmin values in Equation 1, rather than the calculated DPOP (or other FRP) value. That is, the inputs themselves may be scaled or adjusted, and then the scaled DPOP (or other FRP) value may be calculated based on those scaled inputs.

Figures 5A, 5B:
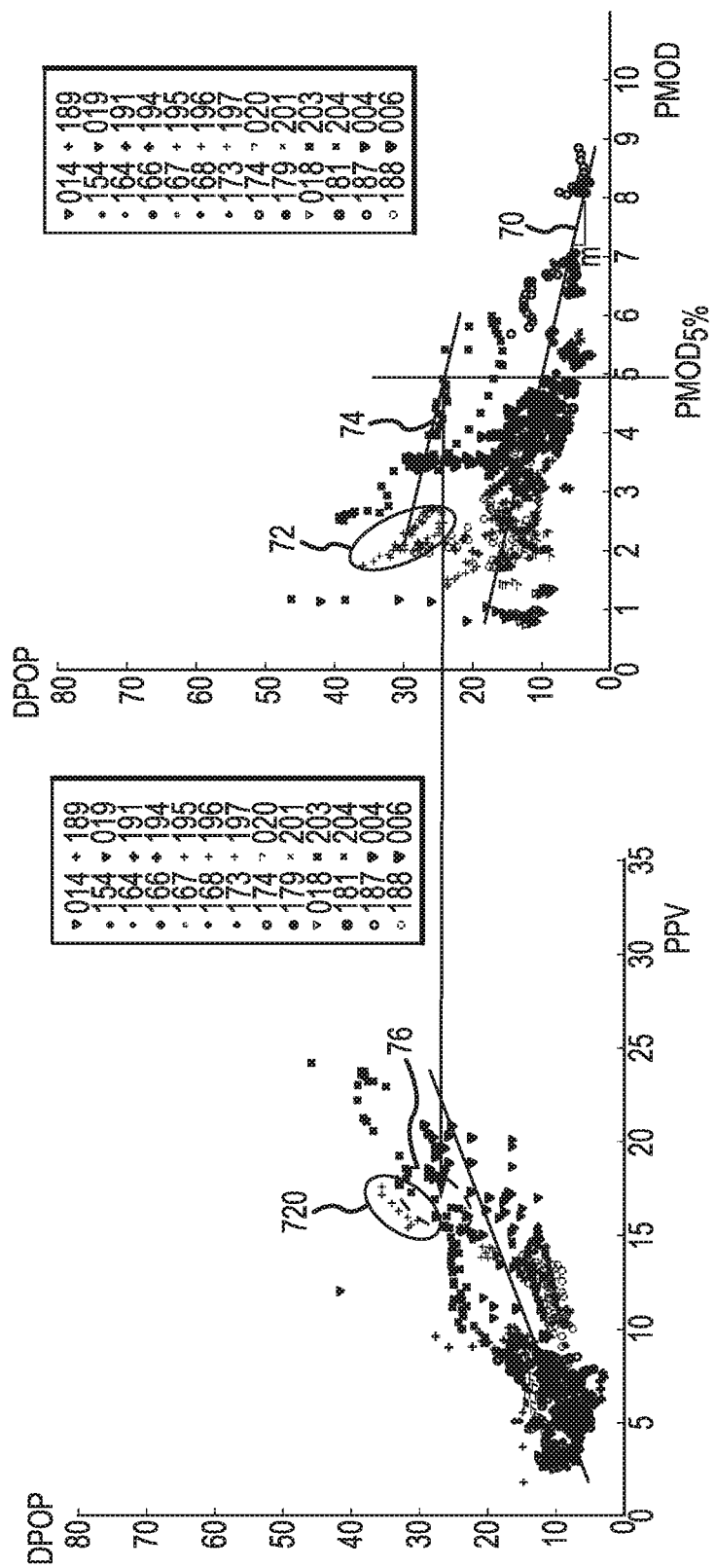
FIG. 5A illustrates a correlation plot of DPOP and PPV, with particular data points noted before and after implementing a correction for low perfusion data, according to an embodiment of the present disclosure.
FIG. 5B illustrates a plot relating DPOP and Pmod for purposes of applying a low perfusion correction to the data of FIG. 5A.

FIGS. 5A and 5B illustrate an example effect of applying a correction factor based on the slope m. FIG. 5A plots the correlation between DPOP (on the vertical axis) and PPV (on the horizontal axis) for a historical data set. FIG. 5B plots DPOP versus Pmod. A best fit line 70 with slope m is fitted to the data points.

A group of data points 72 is identified in FIG. 5B, encompassing a group of DPOP values calculated at a low Pmod of around 2%. These same data points are identified by group 720 in FIG. 5A. A correction factor is applied to these data points to improve the correlation with PPV. Referring to FIG. 5B, the data points 72 are shifted along a line 74 with slope m (the same slope from line 70) to a target Pmod of 5%. This shift reduces the DPOP values from about 30% to about 25% (as shown on the y-axis in FIG. 5B). The corrected DPOP values are then re-plotted in FIG. 5A in group 76. As evident in FIG. 5A, the corrected DPOP group 76 shows improved correlation with PPV as compared with the original outlier group 720. This improvement is notable, as outliers often provide the largest hurdle in the design of clinical algorithms.

Figure 6:
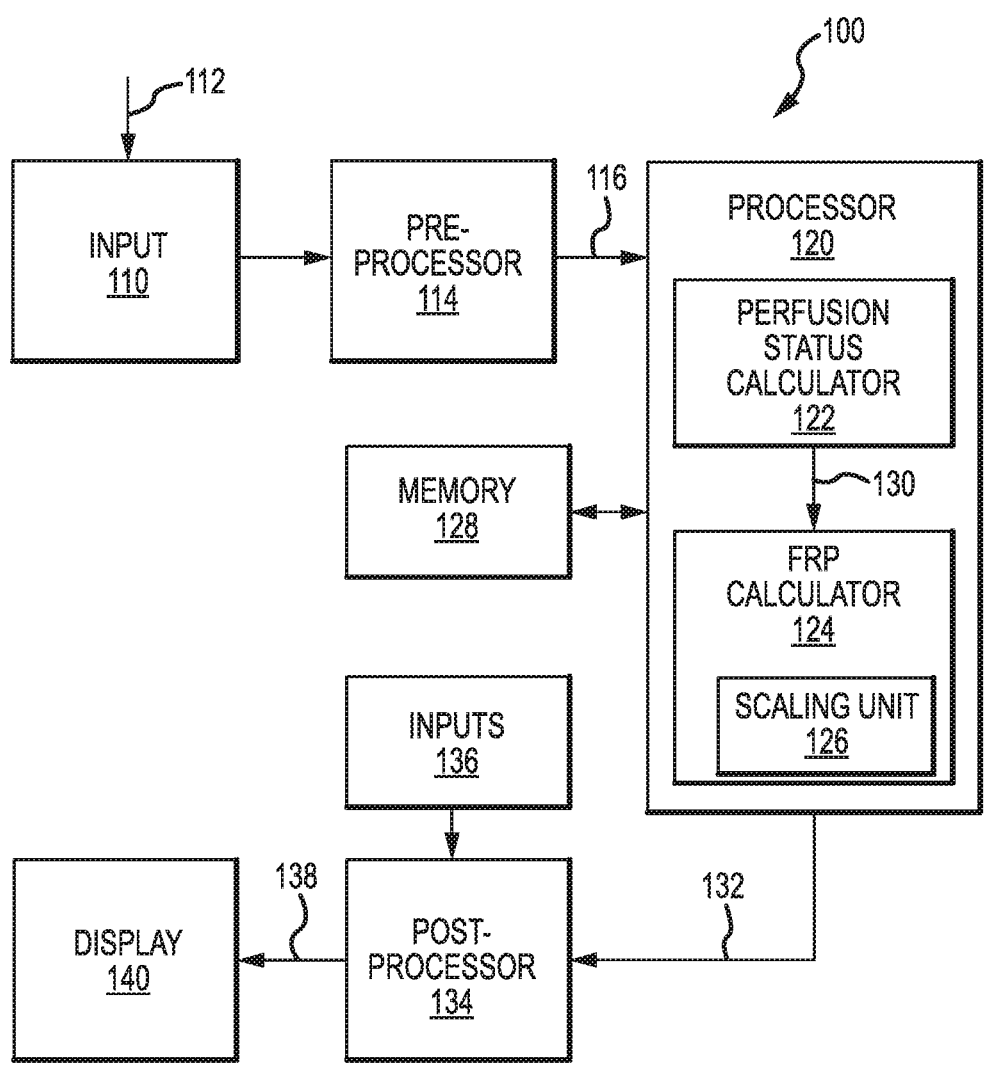
FIG. 6 illustrates a block diagram of a system for determining a fluid responsiveness predictor, according to an embodiment of the present disclosure.

A system 100 for monitoring a patient's vital signs, such as a patient's fluid responsiveness, according to an embodiment, is shown in FIG. 6. The system 100 includes an input 110 that receives a PPG signal 112, such as a raw PPG signal from a sensor applied to the patient. The sensor may be a pulse oximetry sensor applied to a patient's finger, toe, earlobe, or forehead, for example. The input may include a port for wired connection to the sensor, or a wireless receiver for receiving signals wireless from the sensor. The system also includes a pre-processor 114 that initially processes the PPG signal 112. For example, the pre-processor may include one or more filters, such as a low pass filter to remove noise, and/or a filter based on the patient's heart rate to remove irregular pulses. The pre-processor manipulates the incoming PPG signal prior to parameter calculations, such as heart rate, oxygen saturation, or FRP. Pre-processing may also include removing the dichrotic notches 29 (shown in FIG. 1), such as by low pass filtering, adaptive filtering based on heart rate, or removing smaller peaks within a defined proximity, such as 0.35 seconds, to a larger peak. The pre-processor may apply a mapping analysis to identify upstrokes in the PPG signal, such as by looking for peaks in the derivative of the PPG signal to identify separate upstrokes (a derivative fiducial detection method). Signal processing methods for identifying upstrokes and other methods are described in more detail in U.S. application Ser. No. 13/243,951 (U.S. Publication No. 2013/0080489).

The pre-processed PPG signal 116 is then passed to a parameter processor 120. In an embodiment, the processor 120 includes a perfusion status calculator 122 and an FRP calculator 124. The perfusion status calculator 122 takes the incoming PPG signal 116 and calculates a perfusion metric 130. In an embodiment, the perfusion metric 130 is a perfusion status indicator, such as Pmod or a suitable modulation metric.

The FRP calculator 124 takes the PPG signal 116 and calculates an FRP value 132, as discussed above. In an embodiment, the FRP calculator 124 also includes a scaling unit 126, which applies a correction factor, adjustment, or modifier to the FRP value 132 based on the perfusion metric 130. The FRP calculator 124 takes as inputs the PPG signal 116 and the perfusion metric 130. When the perfusion metric 130 indicates a low perfusion status of the patient, the scaling unit 126 adjusts the FRP value accordingly before outputting it as the FRP metric 132.

The system 100 may also include a post-processor 134 which further processes the FRP value 132 to provide a smoothed or processed FRP value 138 prior to displaying it to a caregiver. For example, the post-processor 134 may smooth the FRP value by calculating a running average of the calculated FRP values over a time window. The time window may be chosen by a user for a smoother or faster FRP value (for example, 120 seconds, or 15 seconds, or other similar durations). The post-processor may also remove outlier FRP values before averaging or displaying. For example, when DPOP is the FRP, outlier removal may include removing all DPOP values above 70%, as these values are generally due to noise rather than physiology. For additional smoothing, the post-processor may employ percentile averaging, in which only the middle 50% of calculated FRP values within a time window are added to the running average, and the lowest 25% and highest 25% of values are removed. Additionally, the post-processor may remove particular FRP values due to other conditions that indicate a deterioration in the PPG signal or the patient's condition, such as a signal-to-noise ratio value or an artifact flag (indicating potential artifact in the PPG signal), physiological parameters zero or out of range (for example, blood oxygen saturation or heart rate beyond a particular threshold), or other conditions (for example, arrhythmia present in the signal). The post-processor may also check system settings, and may decide to remove an FRP value due to a system status, such as a gain change in the pulse oximeter, which may cause an abrupt step change in the PPG signal, leading to temporarily skewed FRP values. These various system, signal, and physiological inputs to the post-processor are labeled as inputs 136 in FIG. 6. In an embodiment, if a sufficient number of instantaneous FRP values within the window are set to invalid (for example, a quarter of the values) then the output value may be held for a period of time (for example, 30 seconds). If no new valid values are received then the output FRP value may also be set to invalid.

In an embodiment, the scaling unit 126 is incorporated into the post-processor 134, rather than the parameter processor 120, such that the processed FRP value 138 is corrected for low perfusion. In such a case, the perfusion metric 130 may be inputted to the post-processor 134.

The system 100 also includes a memory 128 that stores data used to apply the low perfusion correction. For example, the memory 128 may store error values (see FIG. 2), or historical data from which expected error can be determined, or the calculated slope m (see FIGS. 4A-C).

The system also includes an output that passes the processed FRP value 138 to a display 140 for displaying the FRP value to a caregiver, such as a doctor or nurse or other clinician, for making clinical decisions about patient care. For example, in an embodiment, an FRP value of 15% is used as a threshold for fluid therapy. If the displayed FRP value is greater than a threshold, such as 15%, then the patient is likely to benefit from fluid therapy. If the displayed FRP value is less than 15%, the patient may not benefit. Based on this determination, fluid administration may be initiated, continued, or ceased. The system 100 of FIG. 6 may provide a prompt on the display 140 when the FRP value crosses this threshold. The FRP value may be used in GDT (goal-directed therapy) to incrementally load the patient until the FRP value indicates that further fluid therapy would not be helpful. The 15% threshold is merely an example, and it is to be understood that the threshold may be greater or less than 15%. Moreover, different thresholds may be used to determine whether individual patients would benefit from fluid administration. According to embodiments herein, a calculated FRP value is able to identify PPV values either side of a defined threshold with high sensitivity and specificity.

Referring again to FIG. 6, the block diagram illustrates modules that represent circuit modules that may be implemented as hardware and/or software. It should be noted that the various components of the system 100 may be connected via wired or wireless connections. The components may be separate from each other, or various combinations of components may be integrated together into a medical monitor or processor, or contained within a workstation with standard computer hardware (for example, processors, circuitry, logic circuits, memory, and the like). The system may include processing devices such as microprocessors, microcontrollers, integrated circuits, control units, memory (such as read-only and/or random access memory), and/or other hardware. One or more system components may be housed within a smart cable, a cable adapter, or the like, with a cable that connects to a sensor, such as a pulse oximetry sensor, at one end. Further, one or more system components may connect to an external device such as a cellular or smart phone, tablet, other handheld device, laptop computer, monitor, or the like that may be configured to receive data from the system and show the data on a display of the device.

The systems and methods described herein may be provided in the form of tangible and non-transitory machine-readable medium or media (such as a hard disk drive, etc) having instructions recorded thereon for execution by a processor or computer. The set of instructions may include various commands that instruct the computer or processor as a processing machine to perform specific operations such as the methods and processes of the various embodiments of the subject matter described herein. The set of instructions may be in the form of a software program or application. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

Figure 7:
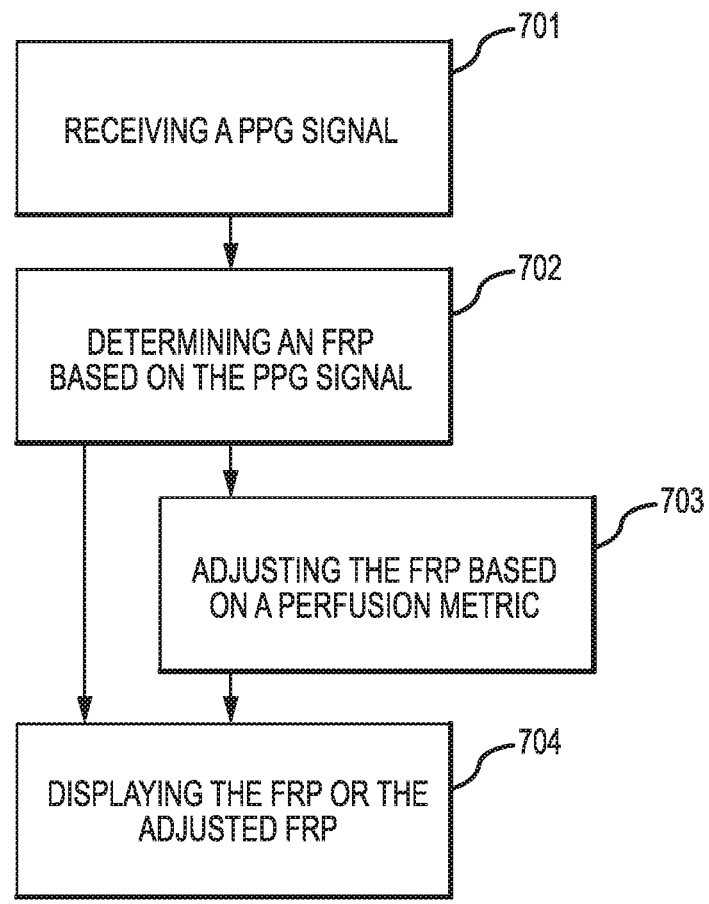
FIG. 7 illustrates a flowchart of a method for determining a fluid responsiveness predictor, according to an embodiment of the present disclosure.

A method for processing a signal to predict a patient's fluid responsiveness, according to an embodiment, is shown in FIG. 7. In the embodiment shown, the method includes receiving a PPG signal 701. The PPG signal is responsive to light emitted into a patient's tissue. The method also includes determining an FRP based on the PPG signal 702. The perfusion status may be a perfusion status indicator, such as a perfusion metric or a modulation metric, for example, Pmod. The FRP may be a variation metric, a respiratory component of the PPG, or DPOP, for example. The method also includes adjusting the FRP value based on the perfusion status 703. For example, when the perfusion status indicates that perfusion is low, the method includes modifying the FRP value, such as by scaling, adjusting, or correcting it, to account for the low perfusion state. In an embodiment, this includes determining an error value at particular perfusion state, and then modifying the FRP based on the error. This modification may be performed only if the perfusion state is below a particular threshold. The method also includes displaying the FRP value or adjusted FRP value 704. Displaying the FRP may include displaying a historical trend of FRP values over time (such as a set or adjustable time window). Such a history of past FRP values may also be stored for patient records or for later review.

Figure 8:
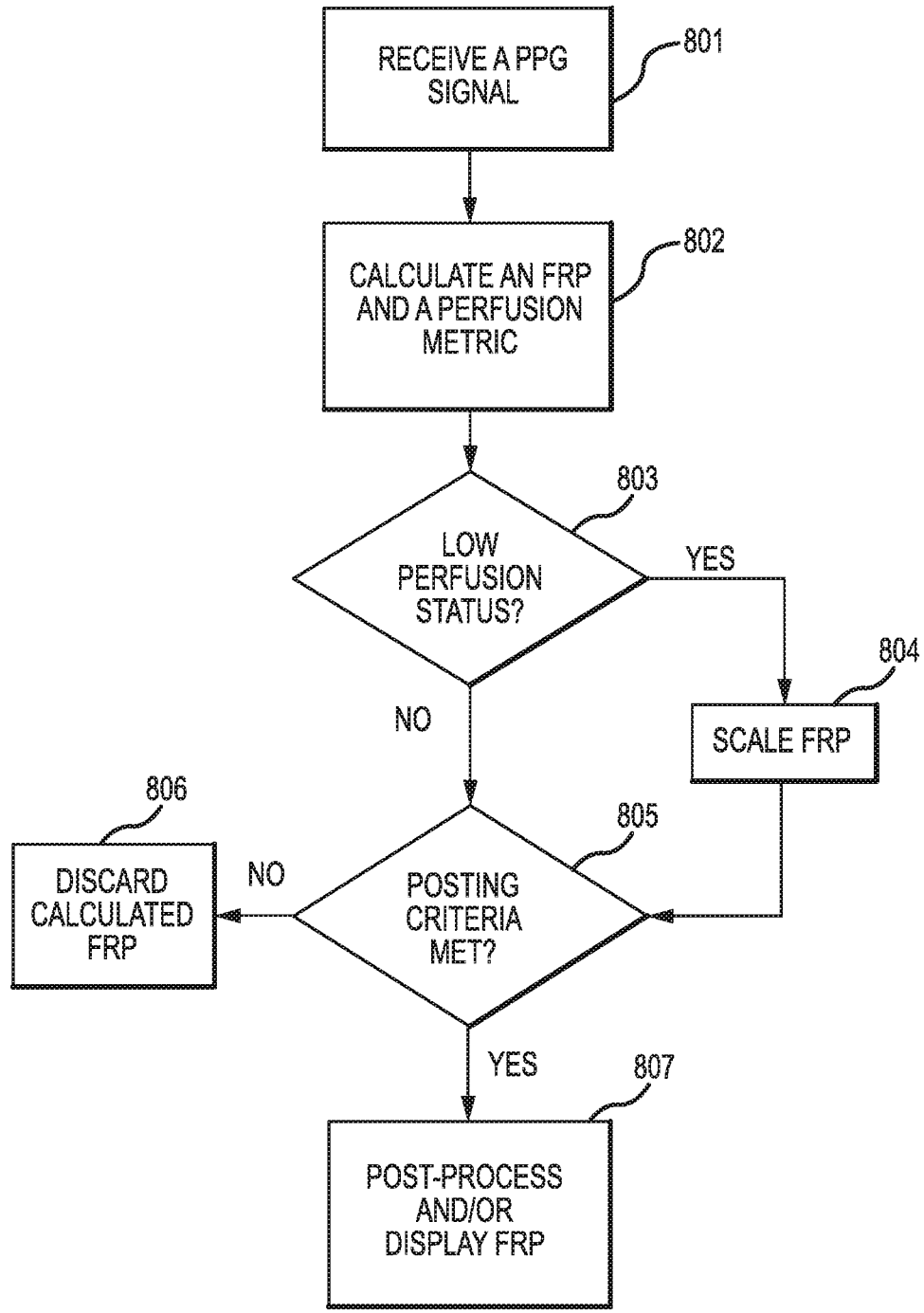
FIG. 8 illustrates a flowchart of a method for determining a fluid responsiveness predictor, according to an embodiment of the present disclosure.

A method of predicting a patient's fluid responsiveness according to an embodiment is shown in FIG. 8. The method includes receiving a PPG signal 801, and calculating an FRP and a perfusion metric 802. In an embodiment the FRP is a PPG-derived variation metric, such as DPOP. In an embodiment, the perfusion metric is a PPG-derived modulation metric, such as Pmod. At 803, a low perfusion status is determined, such as by comparing the perfusion metric to a threshold. If the perfusion metric is above the threshold, then a low perfusion status is not identified. If the perfusion metric is below the threshold, then a low perfusion status is identified, and the method includes scaling the FRP 804.

The method then includes determining whether posting criteria are met at 805. If the posting criteria are not met, the new value of the FRP is discarded at 806. In this case, if previous FRP values met the posting criteria, then the previously calculated FRP value may continue to be displayed. If new values continue to fail the posting criteria, a timer may be incremented until it reaches a threshold, such as 15, 20, 30, 45, or 60 seconds. At that time the previously displayed FRP value may be removed and no value displayed until new data that meets the posting criteria is received. Posting criteria include various checks to assess the likely accuracy of the newly calculated FRP number. Examples of posting criteria include an arrhythmia flag (indicating that cardiac arrhythmia may be present in the PPG signal), a signal-to-noise ratio value or artifact flag (indicating noise is present in the PPG signal), a servo flag (indicating that a recent gain change occurred within the current processing window, which could distort calculations based on the PPG amplitude), system flags (such as sensor off or sensor disconnected), and/or physiologic flags (such as heart rate, respiratory rate, or blood oxygen saturation being out of a specified range, or above or below a threshold). These flags indicate that the FRP number may be distorted by signal degradation or a physiological event. The posting criteria may also include a cap for the FRP number itself; for example if the FRP number exceeds a threshold (such as 70%), then it is not posted.

The FRP value is further post-processed or displayed at 807. This step can include filtering, smoothing, and/or averaging the FRP number, displaying the number, and/or displaying a trend.

In an embodiment, the method of FIG. 8 is called at a specified frequency, such as the duration of a desired time window of PPG data. Over that window of data, the method operates to calculate the FRP and adjust it as necessary. In an embodiment, the method is called every 5 seconds and uses 10 seconds of data, thus incorporating both new and previous data into the data window. Other time windows may be used, and may be adjusted based on a patient's respiration rate. Over time, as new FRP values are calculated, the output may switch between the scaled FRP and the non-scaled FRP values. When the output is averaged over several FRP calculations, the average may include some scaled FRP numbers and some non-scaled FRP numbers. Thus, in an embodiment the method includes using alternative ways to calculate an FRP metric, and combining, selecting, or averaging the alternatively calculated numbers.

In an embodiment, the FRP value, or the inputs to that value, are scaled with a variable scaling based on the patient's perfusion status. That is, the decision block 803 in FIG. 8 is omitted, and the scaling at 804 is applied to the FRP (or its inputs) based on the perfusion metric. When the perfusion metric indicates good perfusion, the amount of scaling is low or negligible or zero. As perfusion decreases, the scaling increases. This adjustment may be done on a continuous or step-wise basis as perfusion changes. The FRP value passed into block 805 is a function of the FRP inputs (such as the amplitudes described above) and the perfusion metric or status.

Figure 9:
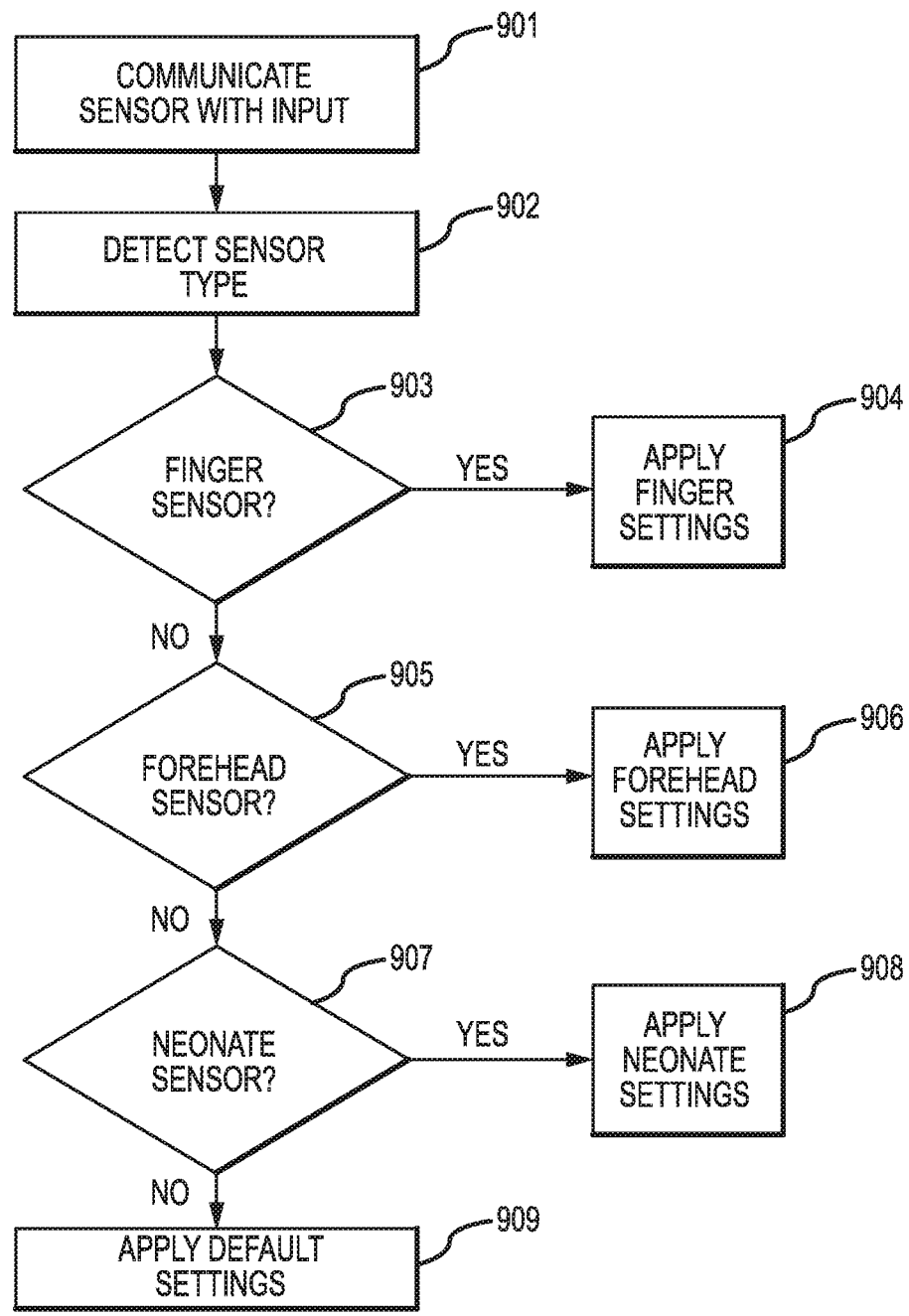
FIG. 9 illustrates a flowchart of a method for determining a fluid responsiveness predictor at various sensor sites, according to an embodiment of the present disclosure.

In an embodiment, the FRP calculation may be adjusted based on the sensor type. Sensor type may include sensors tailored for particular locations on the patient's body (for example, fingers, toes, forehead, or ear), or for certain patient groups (neonates, children, adults). The resulting PPG signals from these various different sensors may exhibit different properties, and as a result, the FRP calculation based on these different PPG signals may be adjusted. A method for adjusting an FRP calculation based on sensor type, according to an embodiment, is shown in FIG. 9. The method includes communicating a sensor with a sensor input, at 901. The method then includes detecting the sensor type, at 902. As noted above, examples of sensor type include forehead, finger, toe, ear, nose, neonate, pediatric, and adult sensors. Information about the sensor type may be stored on the sensor itself (such as a lookup table with coefficients, stored on a memory chip on the sensor or sensor cable), and communicated to the processor when the sensor is connected to the input. That is, the sensor may identify itself as a particular type, and provide the associated settings to the processor for operating the FRP calculation. Alternatively, the processor may determine the sensor type and retrieve the associated settings.

The method then includes choosing the settings associated with the identified sensor type. A few examples are outlined in FIG. 9. For example, the method may include applying finger settings, at 904, if a finger sensor is identified, at 903. As another example, the method may include applying forehead settings, at 906, if a forehead sensor is identified at 905. As another example, the method may include applying neonate settings, at 908, if a neonate sensor is identified at 907. Other sensor types and settings may be included, though they are not all outlined in FIG. 9—such as ear sensors, pediatric sensors, and adult sensors. If no sensor type is identified, the method may include applying default settings, at 909. Default settings may be those for an adult finger sensor, for example.

The settings that are applied for a particular sensor type are settings that adjust the FRP calculation to accommodate differences in the PPG signal from that particular type of sensor. A few examples are outlined next. For a forehead sensor, the settings may include changing the threshold for applying the low perfusion correction to the FRP (such as DPOP). The PPG signal from the forehead tends to be less affected by vasoconstriction than the PPG signal from a finger, and thus may be less affected by low perfusion conditions. Accordingly, when a forehead sensor is detected, the system settings may be adjusted to change the low perfusion threshold, such as lowering it to a Pmod value of 2%, or 1%, or omitting the low perfusion correction entirely (that is, omitting steps 803 and 804 in FIG. 8, when a forehead sensor is detected). Other settings that may be adjusted include the amount or type of pre-filtering, such as the reducing the amount of low-pass filtering on the PPG signal before processing it for FRP calculations.

As another example, when a non-finger sensor is detected (such as a forehead or ear sensor), differences in the resulting PPG signal may scale the FRP calculation, as compared to a finger sensor. The PPG signal from a forehead sensor may exhibit smaller peak-to-peak amplitude, or different respiratory modulations, than a finger sensor, resulting in a different DPOP number, for example. The PPG signal from an ear sensor may exhibit peaks with a more rounded shape, and different amplitudes, than a finger sensor. As a result, the settings for these sensors may include applying an additional scaling factor to scale the DPOP number (or other FRP value) to the number that would result from a finger sensor. This scaling enables a clinician to assess DPOP numbers on the same scale, regardless of which type of sensor is being used. Thus, the clinician may make clinical decisions based on a single DPOP threshold (such as 15%, as described above), without having to change that threshold based on sensor type. A scaling factor can be chosen for each particular sensor type, based on historical patient data, or patient-specific data if available, showing the relationship between DPOP values calculated from a finger sensor and from the particular non-finger sensor. Thus, DPOP values from various sensor types can be mapped to a common scale for display.

As another example, when a neonatal sensor is detected, the settings may be adjusted to provide a different time window for the FRP calculation. As described above, an FRP may be based on the amplitudes or areas of acceptable cardiac pulses within a particular time frame or window. Neonates tend to have a higher pulse rate than adults, and thus this time window may be decreased when a neonate sensor is detected, to reduce the number of cardiac pulses present in the window. Similarly, when a pediatric sensor is detected, the window may also be decreased, to a lesser extent than a for neonate sensor.

Accordingly, an FRP system according to an embodiment includes alternate code modules associated with alternate sensor types. The code modules include different, additional, or fewer steps for the calculation of the FRP parameter, according to the sensor type. A method of calculating an FRP, according to an embodiment, includes adjusting settings (such as thresholds, coefficients, scaling factors, filtering, and other steps) according to a detected sensor type. In an embodiment, the processor checks for the appropriate FRP settings prior to calculating and displaying an FRP value. If no FRP settings are detected on the sensor, then the processor may determine that the sensor is not an authorized or authentic sensor, and may display an appropriate warning message. This check prevents the use of sensors that are not properly calibrated for the FRP signal processing.

Figure 10:
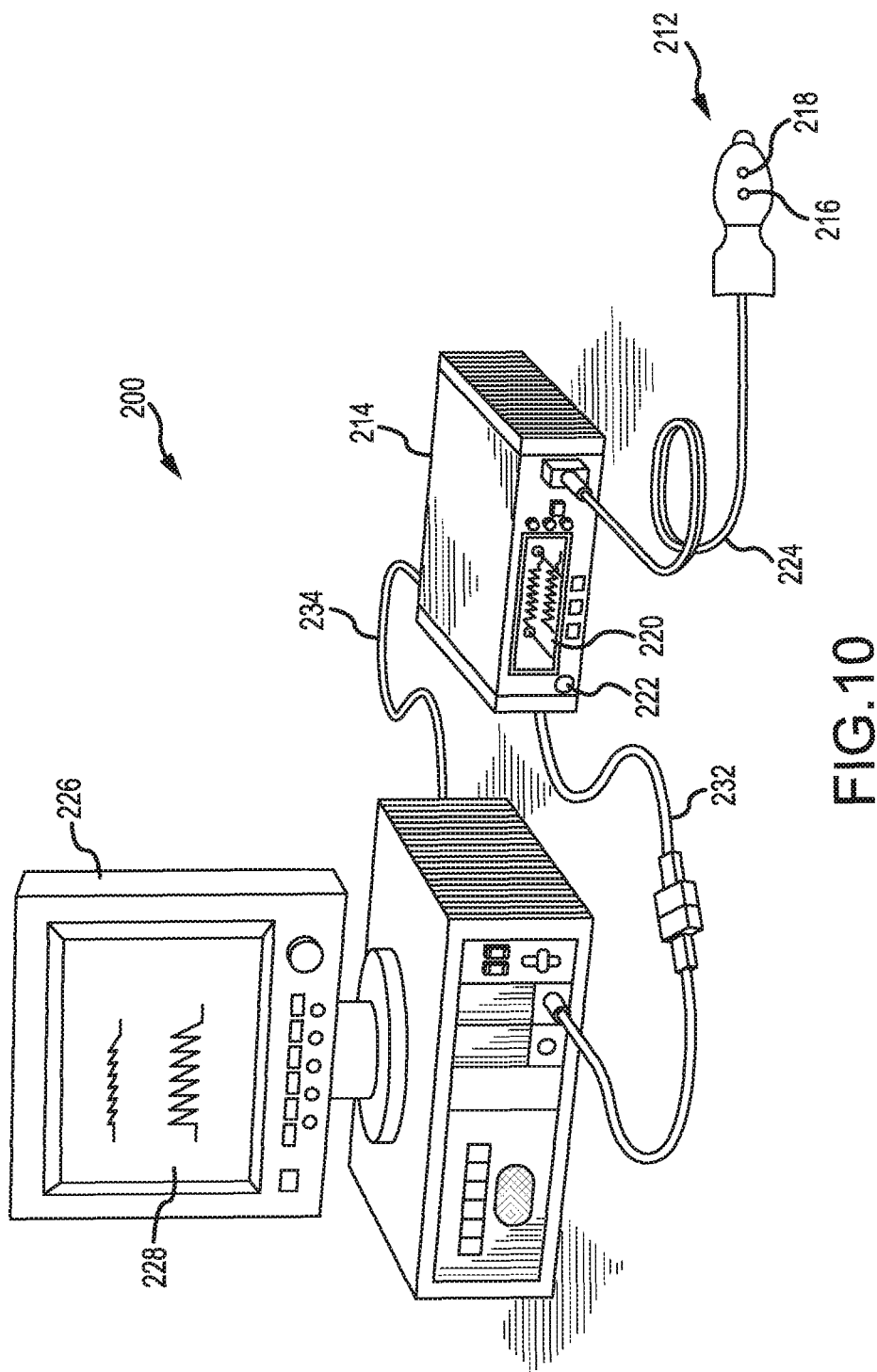
FIG. 10 illustrates an isometric view of a pulse oximetry system, according to an embodiment of the present disclosure.

In an embodiment, the system and methods described above are implemented on a pulse oximeter. A pulse oximeter system 200 is illustrated in FIG. 10. The pulse oximeter non-invasively measures oxygen saturation of hemoglobin in arterial blood, by assessing a ratio of detected light at two wavelengths after illumination into a patient's tissue. For example, the oximeter may measure the intensity of light that is attenuated by the tissue and received at the light sensor, as a function of time. A signal representing light intensity or absorption versus time or a mathematical manipulation of this signal (e.g., a scaled version thereof, a log taken thereof, a scaled version of a log taken thereof, etc.) may be referred to as the photoplethysmograph (PPG) signal. The light intensity or the amount of light absorbed is then used to calculate the amount of a blood constituent (e.g., oxyhemoglobin) as well as the pulse rate and when each individual pulse occurs. To measure a constituent in the blood, the emitted light is selected to be of one or more wavelengths that are absorbed by blood in proportion to the blood constituent. For example, for determination of blood oxygen saturation ($SpO_2$) red and infrared wavelengths are used because highly oxygenated blood absorbs relatively less red light and more infrared light than blood with a lower oxygen saturation. By comparing the intensities of two wavelengths at different points in the pulse cycle, it is possible to estimate the blood oxygen saturation of hemoglobin in arterial blood.

Referring to FIG. 10, the pulse oximetry system 200 includes a sensor or probe 212 and a pulse oximetry monitor 214. The sensor 212 includes an emitter 216 configured to emit light at two or more wavelengths into a patient's tissue, and a detector 218 for detecting the light originally from the emitter 216 after passing through the tissue. The sensor 212 is connected via a cable 224 to the monitor 214, which includes a display 220 to display physiological data and speakers 222 to provide audible alarms. Calculations of physiological parameters from the PPG signal may take place on the sensor and/or the monitor. Optionally, the oximeter monitor 214 may be connected (via cable 232 or 234) to a multi-parameter patient monitor 226, which displays data from various medical devices on a display 228. The calculated FRP value may be displayed on the monitor 214, 226, or both.

Figure 11:
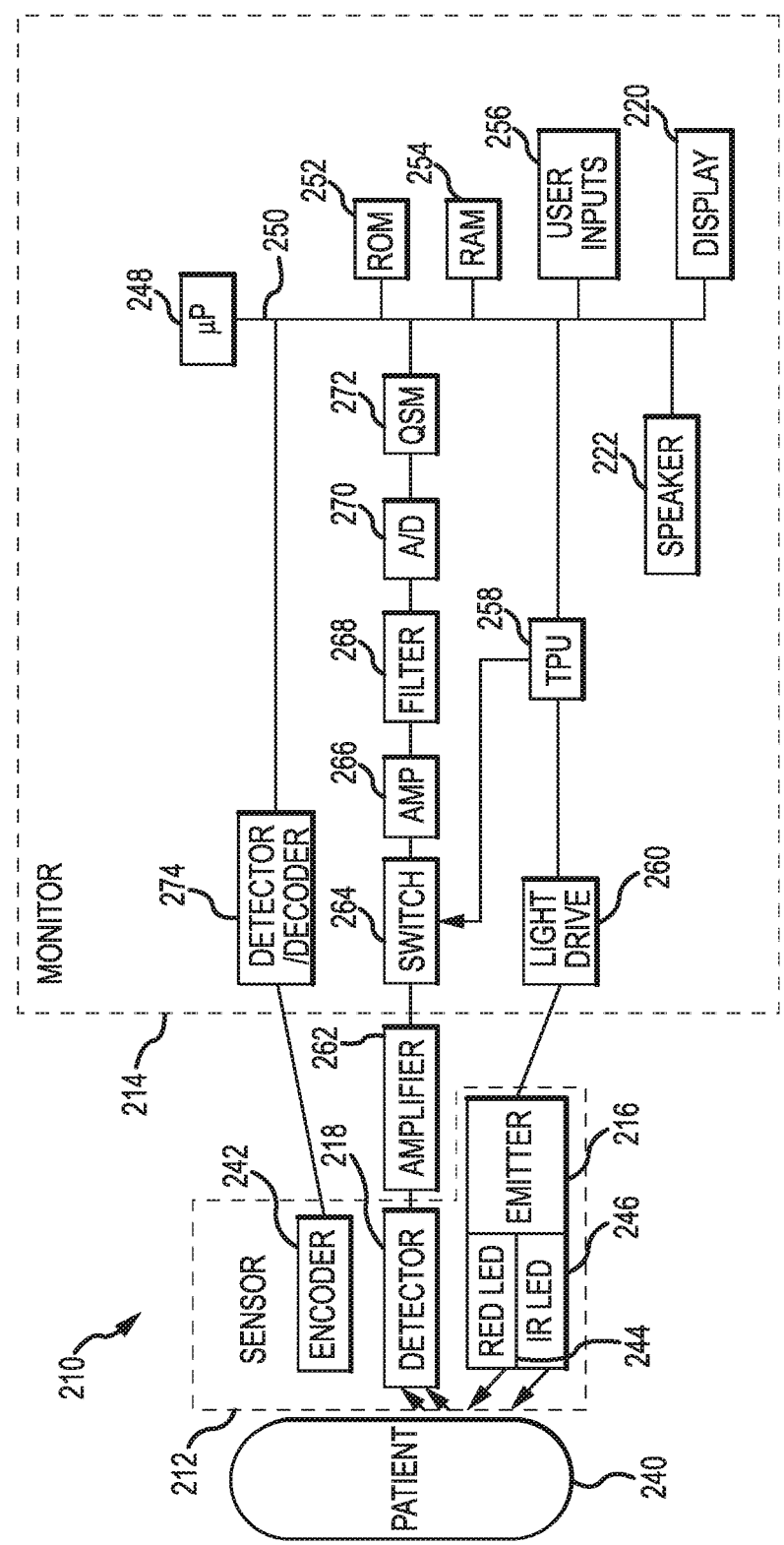
FIG. 11 illustrates a block diagram of a pulse oximetry system, according to an embodiment of the present disclosure.

A simplified block diagram of the system 200 is shown in FIG. 11. Certain illustrative components of the sensor 212 and the monitor 214 are illustrated in FIG. 11. The sensor 212 includes the emitter 216, the detector 218, and an encoder 242. The emitter includes a RED light emitting light source 244, such as a light emitting diode (LED), and an infrared (IR) light emitting light source 246. In at least one embodiment, the RED wavelength may be between about 600 nm and about 700 nm, and the IR wavelength may be between about 800 nm and about 1000 nm. The detector detects light emitted or reflected from the patient's tissue 240, converts the received light into an electrical signal, and sends the signal to the monitor 214. The encoder 242 may contain information about the sensor 212, such as the type of sensor (for example, whether the sensor 212 is intended for placement on a forehead or digit) and the wavelengths of light emitted by the emitter 216. The information may be used by the monitor 214 to select appropriate algorithms, lookup tables and/or calibration coefficients stored in the monitor 214 for calculating the patient's physiological parameters.

The received signal from the detector 218 may be passed through an amplifier 266, a low pass filter 268, and an analog-to-digital converter 270. The digital data may then be stored in a queued serial module (QSM) 272 (or buffer) for later downloading to RAM 254 as QSM 272 fills up.

The monitor 214 includes a general-purpose microprocessor 248 connected to an internal bus 250. Also connected to the bus 250 are a read-only memory (ROM) 252, a random access memory (RAM) 254, user inputs 256 (such as patient information, alarm limits, etc), display 220, and speaker 222. The microprocessor 248 determines the patient's physiological parameters, such as $SpO_2$, respiration rate, respiratory effort, and pulse rate, using various algorithms and/or look-up tables based on the value of the received signals and/or data corresponding to the light received by the detector 218. Information from the encoder 242 is transmitted to a decoder 274, which translates the information to enable the processor 248 to use appropriate thresholds, algorithms, or other information. A time processing unit (TPU) 258 provides timing control signals to a light drive circuitry 260, which controls when the emitter 216 is illuminated and multiplexed timing for the RED LED 244 and the IR LED 246. The TPU 258 may control the sampling of signals from the detector 218 through an amplifier 262 and a switching circuit 264.

It is to be understood that the above description is intended to be illustrative, and not restrictive. Many modifications may be apparent to those skilled in the art to adapt a particular situation or system to the teachings of the present invention, without departing from its scope. The scope of the disclosure should, therefore, be determined with reference to the appended claims, along with the full scope of equivalents to which such claims are entitled.

What is claimed is:

1. A medical monitor for monitoring a subject, the medical monitor comprising:
   a sensor port configured to:
      receive sensor type identification data of a photoplethysmography (PPG) sensor; and
      receive a PPG signal representing light absorption by a subject's tissue from the PPG sensor;

a processor configured to:
  determine a sensor type of the PPG sensor based on the received sensor type identification data;
  choose at least one fluid responsiveness predictor (FRP) calculation setting from a plurality of FRP calculation settings based on the sensor type, each FRP calculation setting of the plurality of FRP calculation settings including a correction factor that improves correlation between PPG signals sensed via the respective sensor type and pulse pressure variation, wherein at least two FRP calculation settings of the plurality of FRP calculation settings comprise different correction factors; and
  calculate an FRP value based on a respiratory variation of the PPG signal, and based on the at least one FRP calculation setting, wherein to calculate the FRP value, the processor is configured to:
    determine a perfusion status of the subject, wherein the perfusion status of the subject is determined based on the sensor type; and
    apply the correction factor from the at least one FRP calculation setting to calculate the FRP value based at least in part on the perfusion status; and
a display configured to display the FRP value.

2. The monitor of claim 1, wherein the sensor type is at least one of: a forehead sensor, a finger sensor, a toe sensor, an ear sensor, a nose sensor, a neonate sensor, a pediatric sensor, or an adult sensor.

3. The monitor of claim 1, wherein the sensor port is configured to receive the sensor type identification data from the PPG sensor.

4. The monitor of claim 1, wherein the sensor port is configured to receive the sensor type identification data via a cable that communicatively connects the PPG sensor and the medical monitor.

5. The monitor of claim 1, wherein the processor is configured to calculate the FRP value based on a difference between a maximum upstroke amplitude and a minimum upstroke amplitude divided by an average of the maximum upstroke amplitude and the minimum upstroke amplitude.

6. The monitor of claim 1, wherein the correction factor includes a low perfusion correction factor, and wherein to calculate the FRP value, the processor is configured to:
  determine that a step of utilizing the low perfusion correction factor to calculate the FRP value should be omitted based on the sensor type; and
  cause the medical monitor to omit the step of applying the low perfusion correction factor when calculating the FRP value.

7. The monitor of claim 1, wherein the processor is configured to:
  calculate the FRP value based on a time window of the PPG signal; and
  modify the size of the time window based on the sensor type.

8. The monitor of claim 1, wherein the correction factor includes one or more of: a threshold adjustment, a correlation coefficient adjustment factor, a sensor type correction factor, a scaling factor, or a filter adjustment factor.

9. The monitor of claim 1, wherein the processor is configured to choose the at least one FRP calculation setting by at least receiving the at least one FRP calculation setting from the PPG sensor.

10. The monitor of claim 1, wherein to calculate the FRP value based on the respiratory variation of the PPG signal, the processor is configured to:
  determine a respiratory-induced modulation of the PPG signal indicative of the respiratory variation of the PPG signal, wherein the respiratory-induced modulation is determined based at least in part on a plurality of amplitude modulations or frequency modulations of an arterial component of the PPG signal or wherein the respiratory-induced modulation is determined based at least in part on a plurality of baseline values of a baseline component of the PPG signal;
  determine the respiratory variation of the PPG signal based at least in part on the respiratory-induced modulation of the PPG signal; and
  calculate the FRP value based at least in part on the respiratory-induced modulation of the PPG signal, and based on the at least one FRP calculation setting.

11. The monitor of claim 1, wherein the PPG signal includes an arterial component and a baseline component, and wherein the perfusion status of the subject is based at least in part on a comparison of the arterial component of the PPG signal and the baseline component of the PPG signal.

12. A medical monitor comprising:
a sensor port configured to:
  receive sensor type identification data of a photoplethysmography (PPG) sensor; and
  receive a PPG signal representing light absorption by a tissue of a subject from the PPG sensor;
a processor configured to:
  determine a sensor type of the PPG sensor based on the received sensor type identification data;
  choose at least one fluid responsiveness predictor (FRP) calculation setting from a plurality of FRP calculation settings based on the sensor type, wherein at least two FRP calculation settings of the plurality of FRP calculation settings comprise different correction factors; and
  calculate an FRP value based on a respiratory variation of the PPG signal, and based on the at least one FRP calculation setting, wherein the FRP value is scaled based on the at least one FRP calculation setting; and
a display configured to display the FRP value.

13. A medical monitor comprising:
a sensor port configured to:
  receive sensor type identification data of a photoplethysmography (PPG) sensor; and
  receive a PPG signal representing light absorption by tissue of a subject from the PPG sensor;
a processor configured to:
  determine a sensor type of the PPG sensor based on the received sensor type identification data;
  choose at least one fluid responsiveness predictor (FRP) calculation setting from a plurality of FRP calculation settings based on the determined sensor type, wherein at least two FRP calculation settings of the plurality of FRP calculation settings comprise different correction factors; and
  calculate an FRP value based on a respiratory variation of the PPG signal, and based on the at least one FRP calculation setting, wherein to calculate the FRP value, the processor is configured to:
    determine a perfusion status of the subject, the perfusion status being one of a low perfusion status or a good perfusion status; and
    apply the correction factor from the at least one FRP calculation setting based at least in part on the perfusion status; and
a display configured to display the FRP value.

14. A method for monitoring vital signs of a subject, the method comprising:
receiving, using a sensor port of a medical monitor, sensor type identification data of a photoplethysmograph (PPG) sensor;
receiving, using the sensor port of the medical monitor, a PPG signal from the PPG sensor;
determining, using a processor of the medical monitor, a sensor type of the PPG sensor based on the received sensor type identification data;
choosing, using the processor of the medical monitor, at least one fluid responsiveness predictor (FRP) calculation setting from a plurality of FRP calculation settings based on the sensor type, each FRP calculation setting of the plurality of FRP calculation settings including a correction factor that improves correlation between PPG signals sensed via the respective sensor type and pulse pressure variation, wherein at least two FRP calculation settings of the plurality of FRP calculation settings comprise different correction factors;
calculating, using the processor of the medical monitor, an FRP value based on a respiratory variation of the PPG signal, and based on the at least one FRP calculation setting, wherein calculating the FRP value comprises:
determining, using the processor of the medical monitor, a perfusion status of the subject, wherein the perfusion status of the subject is determined based on the sensor type; and
applying, using the processor of the medical monitor, the correction factor from the at least one FRP calculation setting to calculate the FRP value based at least in part on the perfusion status; and
displaying, using a display of the medical monitor, the FRP value.

15. The method of claim 14, wherein the sensor type is at least one of: a forehead sensor, a finger sensor, a toe sensor, an ear sensor, a nose sensor, a neonate sensor, a pediatric sensor, or an adult sensor.

16. The method of claim 14, wherein receiving the sensor type identification data comprises receiving the sensor type identification data via a cable that communicatively connects the PPG sensor and the medical monitor.

17. The method of claim 14, wherein calculating the FRP value comprises calculating the FRP value based on a difference between a maximum upstroke amplitude and a minimum upstroke amplitude divided by an average of the maximum upstroke amplitude and the minimum upstroke amplitude.

18. The method of claim 14, wherein the correction factor includes a low perfusion correction factor, and wherein calculating the FRP value comprises:
not applying the low perfusion correction factor based at least in part on the sensor type.

19. The method of claim 14, wherein the method further comprises:
calculating the FRP value based on a time window of the PPG signal, and
modifying, using the processor of the medical monitor, the size of the time window based on the sensor type.

20. The method of claim 14, wherein the PPG signal includes an arterial component and a baseline component, and wherein the perfusion status of the subject is based at least in part on a comparison of the arterial component of the PPG signal and the baseline component of the PPG signal.

* * * * *